(12) United States Patent
Wu et al.

(10) Patent No.: US 10,024,820 B2
(45) Date of Patent: Jul. 17, 2018

(54) MICROFLUIDIC DEVICE FOR GEL ELECTROPHORESIS AND METHOD OF MANUFACTURING THEREOF

(71) Applicant: AGENCY FOR SCIENCE, TECHNOLOGY AND RESEARCH, Singapore (SG)

(72) Inventors: Ruige Wu, Singapore (SG); Zhiping Wang, Singapore (SG); Sai Kiang Lim, Singapore (SG); Yen Peng Daphne Seah, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 273 days.

(21) Appl. No.: 14/658,088

(22) Filed: Mar. 13, 2015

(65) Prior Publication Data

US 2015/0260682 A1   Sep. 17, 2015

(30) Foreign Application Priority Data

Mar. 14, 2014   (SG) ............................ 10201400678Q

(51) Int. Cl.
G01N 27/447 (2006.01)
B65B 3/04 (2006.01)

(52) U.S. Cl.
CPC ......... *G01N 27/44791* (2013.01); *B65B 3/04* (2013.01); *G01N 27/44782* (2013.01)

(58) Field of Classification Search
CPC ........ G01N 27/44782; G01N 27/44791; B65B 3/04
See application file for complete search history.

(56) References Cited

U.S. PATENT DOCUMENTS

2013/0266956 A1*  10/2013  Tia .................... G01N 33/543
                                                               435/7.1

OTHER PUBLICATIONS

R. Wu, et al. "2-D t-ITP/CZE determination of clinical urinary proteins using a microfluidic chip capillary electrophoresis device" Electrophoresis, vol. 32, 2011, p. 3406-3414.*

Efraim Racker, "SDS-PAGE 'Hall of Shame'", Experimental Biosciences—Resources for Introductory & Intermediate Level Laboratory Courses, Rice University, retrieved from the Internet on May 13, 2015: http://www.ruf.rice.edu/~bioslabs/studies/sds-page/sdsgoofs.html, 4 pages, created on Oct. 9, 1996 and updated on Nov. 28, 2006.

* cited by examiner

*Primary Examiner* — J. Christopher Ball
(74) *Attorney, Agent, or Firm* — Womble Bond Dickinson (US) LLP

(57) ABSTRACT

According to embodiments of the present invention, a microfluidic device for gel electrophoresis is provided. The microfluidic device includes a sample channel configured to receive a sample; a stacking channel comprising a preloaded stacking reagent; and a separation channel comprising a preloaded separation reagent, wherein the preloaded stacking reagent has a physical characteristic different from that of the preloaded separation reagent; and wherein the sample channel, the stacking channel and the separation channel are in fluid communication with one another. According to further embodiments of the present invention, a method of manufacturing a microfluidic device for gel electrophoresis is also provided.

17 Claims, 10 Drawing Sheets

(i)

(ii)

(i)

(ii)

MICROFLUIDIC DEVICE FOR GEL ELECTROPHORESIS AND METHOD OF MANUFACTURING THEREOF

CROSS-REFERENCE TO RELATED APPLICATION

This application claims the benefit of priority of Singapore patent application No. 10201400678Q, filed 14 Mar. 2014, the content of it being hereby incorporated by reference in its entirety for all purposes.

TECHNICAL FIELD

Various embodiments relate to a microfluidic device for gel electrophoresis and a method of manufacturing a microfluidic device for gel electrophoresis.

BACKGROUND

Polyacrylamide gel electrophoresis (PAGE) is a technique widely used to separate biological molecules, for example, proteins, by their size, hence, mobility in an electric field. When sodium dodecyl sulfate (SDS) is used to denature the proteins and the polyacrylamide gel is used as a support medium, this method is referred to as SDS-PAGE. A typical set-up of SDS-PAGE is illustrated in FIG. 1.

Protein separation by SDS-PAGE may be used to estimate relative molecular weight (MW) of an unknown protein or determine relative abundance of proteins in a sample. The relationship between mobility (x, the relative distance travelled in a given amount of time) and molecular weight (MW) may be represented by a linear or nearly linear equation of:

$$\text{Log } MW = -mx + b \quad \text{(Equation 1)}$$

where m is the slope and b is the Log MW-intercept.

Preparation of SDS-PAGE requires casting two layers of acrylamide gel between glass plates 102. As seen in the schematic diagram 100 of FIG. 1, the bottom layer, also known as a separation gel 104 is responsible for separating proteins by size, while the top layer, known as a stacking gel 106 includes sample wells 108. A positive electrode 110 of an electrical source (not shown in FIG. 1) is placed toward one end of the acrylamide gel that is at the separation gel 104, while a negative electrode 112 of the electrical source is placed toward the opposite end of the acrylamide gel that is near the sample wells 108 at the stacking gel 106. A moving boundary sweeps proteins 114, 116 in a sample, compressing (stacking) these proteins 114, 116 into thin layers (for example, micrometer thin layers) at the stacking gel 106 before these proteins 114, 116 reach the separation gel 104. When the electrical field is applied across the positive electrode 110 and the negative electrode 112 over the two layers 104, 106 in a buffer solution 118, the proteins 114, 116 move into the separation gel 104 with the smaller proteins 114 moving faster and the larger proteins 116 moving slower toward the positive electrode 110.

Manual gel casting for SDS-PAGE is time-consuming (usually more than 3 hours) and often leads to inconsistent results. For example, common problems due to inappropriate operation of manual gel casting may include unevenly poured acrylamide mixture resulting in smeared gel, light bands from poorly formed wells during gel casting, and others. Moreover, a number of reagents used for gel casting may be toxic. For instance, the main component of acrylamide is a potent neurotoxin and requires careful handling.

Another problem with conventional SDS-PAGE is that it usually requires large amount of expensive reagents in each test due to the size of gel casting jig and gel electrophoresis tank. On the other hand, use of commercially available precast gels may be able to reduce the researchers' invested time and to some extent, minimize the problems of manual preparation of gel. However, such precast gels are generally more expensive when compared to manual gel casting, and this may impact a laboratory's budget and running cost.

Thus, there is a need for a gel electrophoresis device that is cost effective, ready-to-use and user-friendly to address at least the problems above.

SUMMARY

According to an embodiment, a microfluidic device for gel electrophoresis is provided. The microfluidic device may include a sample channel configured to receive a sample; a stacking channel comprising a preloaded stacking reagent; and a separation channel comprising a preloaded separation reagent, wherein the preloaded stacking reagent has a physical characteristic different from that of the preloaded separation reagent; and wherein the sample channel, the stacking channel and the separation channel are in fluid communication with one another.

According to an embodiment, a method of manufacturing a microfluidic device for gel electrophoresis is provided. The method may include providing a microfluidic device comprising: a sample channel configured to receive a sample; a stacking channel; and a separation channel, wherein the sample channel, the stacking channel and the separation channel are in fluid communication with one another; loading the stacking channel with a liquid stacking reagent to form a preloaded stacking reagent; and loading the separation channel with a liquid separation reagent to form a preloaded separation reagent, wherein the preloaded stacking reagent has a physical characteristic different from that of the preloaded separation reagent.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Figure 1:
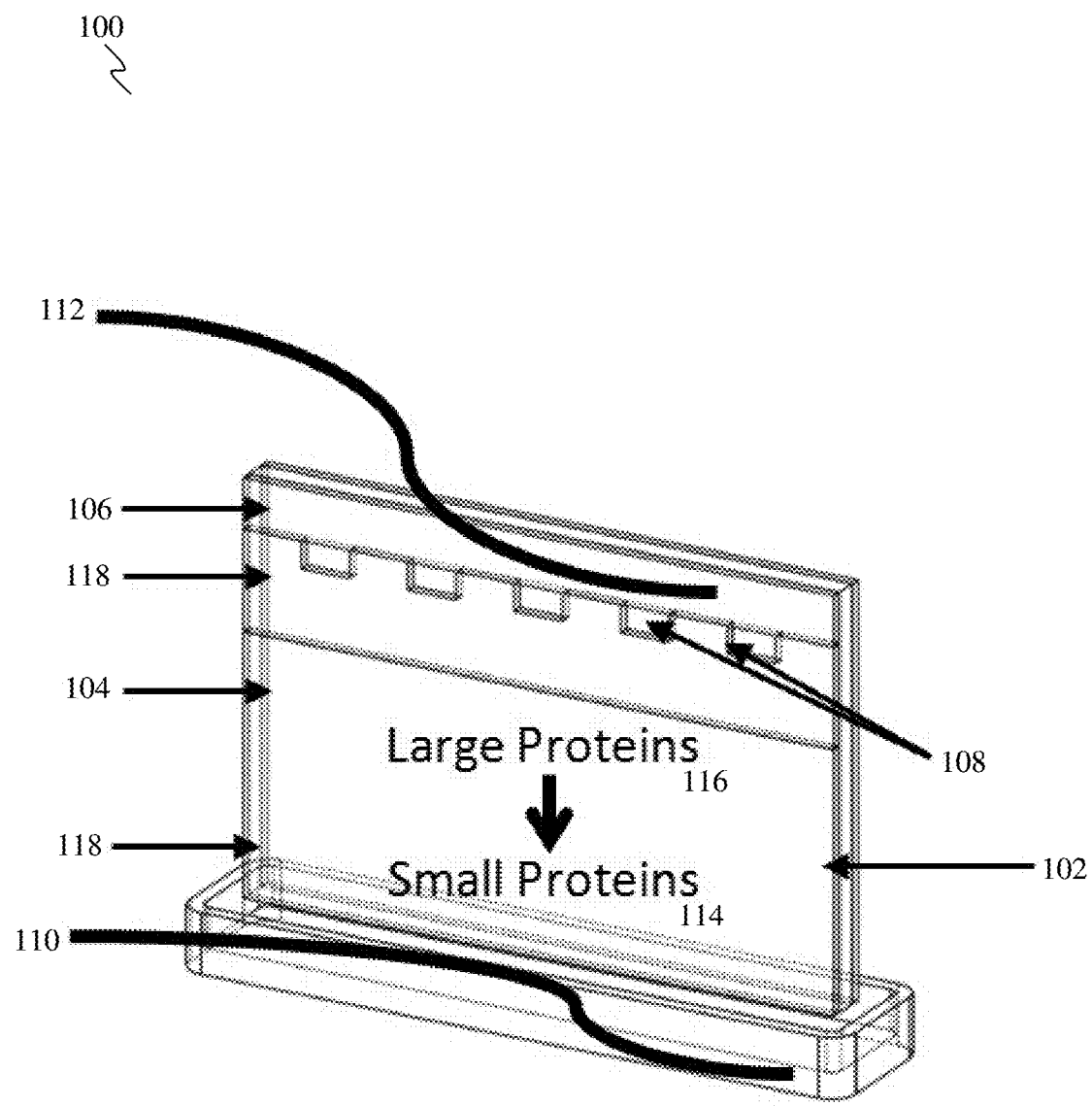
FIG. 1 shows a schematic view of conventional SDS-PAGE.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may provide an on-chip gel electrophoresis device and its manufacturing method.

Various embodiments may relate to a microfluidic chip that is preloaded with reagents and ready to perform gel electrophoresis.

Various embodiments may provide a microfluidic chip for realizing the procedure of conducting SDS-PAGE in a typical gel box, with preloaded gel and/or other reagents. With this configuration, an operator may only need to load the test sample into the microfluidic device before running gel electrophoresis.

Various embodiments may provide a microfluidic chip for gel electrophoresis, consisting of: at least two electrical contact points; a running buffer gel channel filled with running buffer gel; a sample channel for loading samples; a stacking channel preloaded with stacking reagent; a separation channel preloaded with stacking reagent; and the said running buffer gel channel, sample channel, stacking channel, and separation channel are being linked together mechanically and electrically when the sample is loaded.

Figure 2A:
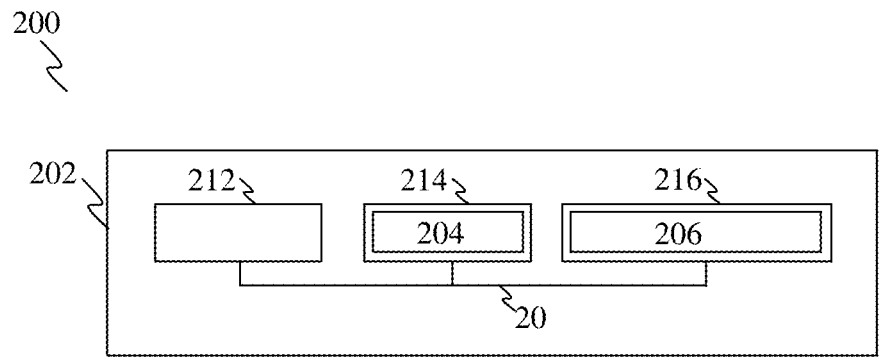
FIG. 2A shows a schematic view of a microfluidic device for gel electrophoresis, according to various embodiments.

FIG. 2A shows a schematic view 200 of a microfluidic device 202 for gel electrophoresis, according to various embodiments. The microfluidic device 202 includes a sample channel 212 configured to receive a sample, a stacking channel 214 including a preloaded stacking reagent 204, and a separation channel 216 including a preloaded separation reagent 206. The preloaded stacking reagent 204 has a physical characteristic different from that of the preloaded separation reagent 206. The sample channel 212, the stacking channel 214 and the separation channel 216 are in fluid communication with one another, as denoted by a line 20 which may represent fluid coupling, or physical coupling, or mechanical coupling among the sample channel 212, the stacking channel 214 and the separation channel 216.

In other words, the microfluidic device 202 may include a sample channel 212 in which a sample may be loaded, for example, by means of a pipette. The sample channel 212 may have a body that may be at least partially exposed to receive the sample to be loaded. For example, the sample channel 212 may be a recess disposed on the microfluidic device 202. The microfluidic device 202 may also include a stacking channel 214 preloaded with a stacking reagent and a separation channel 216 preloaded with a separation reagent, in which the loaded sample traverses during gel electrophoresis. As compared to the conventional SDS-PAGE (FIG. 1) where various components are arranged in a top-down (vertical) configuration such that a loaded sample may diffuse from the sample wells 108 toward the separation gel 104 along a downward direction based on gravitational forces and electrical forces when an electrical potential is applied, the loaded sample in the microfluidic device 202 may traverse differently. More specifically, the sample channel 212, the stacking channel 214, and the separation channel 216 of the microfluidic device 202 may be arranged in a lateral (horizontal) configuration such that the loaded sample traverses through each of the sample channel 212, the stacking channel 214, and the separation channel 216 along a direction that is at least substantially perpendicular to the abovementioned downward direction.

Further, the preloading of the stacking reagent and the separation reagent into the respective stacking channel 214 and separation channel 216 may be carried out, for example, during the manufacturing stages of the microfluidic device 202, thereby allowing the microfluidic device 202 to be ready-to-use, without a need for an operator (user) to separately prepare and apply any stacking reagents or separation reagents for gel electrophoresis prior to and/or when using the microfluidic device 202 for gel electrophoresis.

In various embodiments, the microfluidic device 202 for gel electrophoresis may be used to separate molecules such as DNA, RNA and proteins in samples.

In an example of carrying out protein separation using the microfluidic device 202, the loaded sample may flow into the stacking channel 214 preloaded with the stacking reagent. The stacking channel 214 including the preloaded stacking reagent 204 may allow the proteins in the loaded sample to be concentrated into a tight band during the first few minutes of electrophoresis before entering the separation channel 216 including the preloaded separation reagent 206. This way, optimal resolution of the proteins may be obtained when the proteins are separated into protein bands in the separation channel 216 preloaded with the separation reagent. To accommodate the separate protein bands, the separation channel 216 including the preloaded separation reagent 206 may be longer than the stacking channel 214 including the preloaded stacking reagent 204.

In the context of various embodiments, each of the sample channel 212, the stacking channel 214 and the separation channel 216 may be in the micrometer scale and may be interchangeably referred to as a sample microchannel, a stacking microchannel, and a separation microchannel, respectively. The microfluidic device 202 may be of a substantially smaller scale as compared to the apparatus for the conventional SDS-PAGE.

The stacking channel 214 may be defined as having a tubular body with a cross-section perpendicular to the longitudinal axis of the stacking channel 214 where the cross-section may be at least substantially rectangular, or at least substantially square-shaped, or elliptical, or circular. The longitudinal axis of the stacking channel 214 may be oriented along a direction of sample flow (fluid flow) through the stacking channel 214.

The separation channel 216 may be defined as having a tubular body with a cross-section perpendicular to the longitudinal axis of the separation channel 216 where the cross-section may be at least substantially rectangular, or at least substantially square-shaped, or elliptical, or circular. The longitudinal axis of the separation channel 216 may be oriented along a direction of sample flow (fluid flow) through the separation channel 216.

In the context of various embodiments, the stacking channel 214 is distinct from the separation channel 216 and/or the sample channel 212. In other words, the stacking channel 214 is separate from the separation channel 216 and/or the sample channel 212, and does not form a unitary element with the separation channel 216 and/or the sample channel 212. The separation channel 216 is also distinct from the sample channel 212. In other words, the separation channel 216 is separate from the sample channel 212, and does not form a unitary element with the sample channel 212.

With separate stacking channel and separation channel, the respective reagents may be pre-filled into the respective channels before solidified. If a stacking channel and a separation channel share the same channel, different liquid reagents loaded to the channel would be mixed together before at least one is solidified. Moreover, once one type of loaded reagent (e.g., stacking gel) is solidified, the other reagent cannot be loaded into the same channel as the channel is blocked. This is different from the conventional SDS-PAGE, in which the gels are exposed to air (the atmospheric environment).

In various embodiments, each of the stacking channel 214 and the separation channel 216 may be a closed channel that is prevented from exposure to air. In other words, each of these channels may be concealed within the microfluidic device 202 or in a body of the microfluidic device 202, and thus, the respective reagents loaded into these channels may not be in direct contact with the atmospheric environment.

In the context of various embodiments, the term "physical characteristic" may refer to a pH level or an average pore size.

In various embodiments, the preloaded stacking reagent 204 is different from the preloaded separation reagent 206. In other words, the formulation of the preloaded stacking reagent 204 may be different from the formulation of the preloaded separation reagent 206. More specifically, the preloaded stacking reagent 204 may have the physical characteristic of at least one of a pH level or an average pore size different from that of the preloaded separation reagent 206.

For example, the preloaded separation reagent 206 may have a smaller average pore size and/or a higher pH level as compared to the preloaded stacking reagent 204. Such physical characteristics allow for the preloaded separation reagent 206 to perform separations into bands, and for the preloaded stacking reagent 204 to perform stacking.

In a non-limiting example, the preloaded separation reagent 206 may have a pH level of about 8.8 and the preloaded stacking reagent 204 may have a pH level of about 6.8. The average pore size of the preloaded separation reagent 206 may about 5 times to about 10 times smaller than the average pore size of the preloaded stacking reagent 204.

In various embodiments, each of the preloaded stacking reagent 204 and the preloaded separation reagent 206 may include a polymerized compound. For example, the polymerized compound may include but is not limited to acrylamide or agarose.

In the context of various embodiments, the preloaded stacking reagent 204 may include or may mean a preloaded stacking gel; and the preloaded separation reagent 206 may include or may mean a preloaded separation gel.

In various embodiments, the microfluidic device 202 may further include a plurality of layers, wherein the stacking channel 214 and the separation channel 216 may be arranged on different layers of the plurality of layers.

The stacking channel 214 may be an elongated recess or through-hole disposed on a layer of the plurality of layers. In a different example, the stacking channel 214 may be a tunnel or a channel embedded in this layer. Similarly, the separation channel 216 may be an elongated recess or through-hole disposed on another layer of the plurality of layers. In a different example, the separation channel 216 may be a tunnel or a channel embedded in this other layer.

For example, the separation channel 216 may be arranged on an upper layer and the stacking channel 214 may be arranged on a lower layer; and wherein the upper layer is arranged over the lower layer. The sample channel 212 may also be arranged on the upper layer. In other words, the lower layer may be underneath the upper layer. The upper layer and the lower layer may be coupled to each other using thermal bonding, laser welding, adhesive bonding, and any other suitable methods. It may be appreciated and understood that other arrangements of the channels in different layers may be also possible.

With such arrangements, a liquid stacking reagent may be controllably pre-filled into the stacking channel 214 only, as the liquid stacking reagent would move along a direction of the stacking channel 214 with lower resistance, as compared to flowing into other channels such as the sample channel 212 and the separation channel 216. Once the stacking reagent is solidified, a separation reagent may only be pre-filled into the separation channel 216 since the stacking channel 214 is blocked by the solidified stacking reagent therein.

Each of the plurality of layers may be a planar structure positioned along a plane substantially parallel to the longitudinal axis of the stacking channel 214 and/or the longitudinal axis of the separation channel 216.

In various embodiments, the stacking channel 214 and the separation channel 216 may be fluidly connected to each other by a through-hole.

The through-hole may include a rectangle-shaped through-hole arranged lengthwise across a width of the separation channel 216. Since the rectangle-shaped through-hole may be used to fluidly connect the stacking channel 214 and the separation channel 216, the rectangle-shaped through-hole may also be arranged lengthwise across a width of the stacking channel 214. For example, the rectangle-shaped through-hole may be narrow and may have a width in a range of about 50 µm to about 500 µm.

In various embodiments, the stacking channel 214 and the separation channel 216 may be arranged downstream with respect to the sample channel 212. In other words, when in use, a loaded sample may flow out of the sample channel 212 and toward the stacking channel 214 and the separation channel 216.

In various embodiments, the stacking channel 214 may be arranged between the sample channel 212 and the separation channel 216. In other words, when in use, a loaded sample may flow out of the sample channel 212 and into the stacking channel 214, and then out of the stacking channel 214 and subsequently into the separation channel 216.

In various embodiments, the microfluidic device 202 may further include a first pair of reservoirs in fluid communication with the stacking channel 214; and a second pair of reservoirs in fluid communication with the separation channel 216, wherein the first pair of reservoirs may be configured to provide a first inlet and a first outlet for a liquid stacking reagent to be loaded in the stacking channel 214 to form the preloaded stacking reagent 204; and wherein the second pair of reservoirs may be configured to provide a second inlet and a second outlet for a liquid separation reagent to be loaded in the separation channel 216 to form the preloaded separation reagent 206.

The liquid stacking reagent may be loaded through the first inlet and into the stacking channel 214 by using a pipette. Once the stacking channel 214 is filled, the first outlet may allow the excess liquid stacking reagent to flow out of the stacking channel 214. Similarly, the liquid separation reagent may be loaded through the second inlet and into the separation channel 216 by using a pipette. Once the separation channel 216 is filled, the second outlet may allow the excess liquid separation reagent to flow out of the separation channel 216.

The through-holes may be filled up with the respective reagents due to capillary force during the loading or filling process.

In various embodiments, the microfluidic device 202 may further include a buffer channel comprising a running buffer reagent, wherein the buffer channel may be in fluid communication with the sample channel 212.

The sample channel 212 may be arranged between the buffer channel and the stacking channel 214. In other words, the buffer channel and the sample channel 212 may be arranged upstream with respect to the stacking channel 214.

Air bubbles are usually be generated by electrolysis around electrodes used for electrophoresis. If a bubble enters the sample channel 212, the stacking channel 214 or the separation channel 216, it may cause an electrical circuit supporting the electrophoresis to break down and discontinue gel electrophoresis. Solidified running buffer gel in the buffer channel may prevent any bubble from entering these channels (the sample channel 212, the stacking channel 214 and the separation channel 216). Furthermore, the sample channel 212 may work as a partition between the stacking channel 214 and the buffer channel to isolate the different pre-filled reagents before the microfluidic device 202 is used by an end user for electrophoresis.

In various embodiments, the microfluidic device 202 may further include a plurality of layers, wherein the buffer channel and the sample channel 212 may be arranged on different layers of the plurality of layers.

The sample channel 212 may be arranged on a first layer of the plurality of layers, and the buffer channel may be arranged on a second layer of the plurality of layers; and wherein the first layer may be arranged over the second layer. In other words, the second layer may be underneath the first layer. The first layer and the second layer may be coupled to each other using thermal bonding, laser welding, adhesive bonding, and any other suitable methods.

Accordingly, the buffer channel and the stacking channel 213 may preferably be below the sample channel 212.

With such arrangements, a liquid running buffer reagent may be controllably pre-filled into the buffer channel only, as the liquid running buffer reagent would move along a direction of the buffer channel with lower resistance, as compared to flowing into other channels such as the sample channel 212.

In an example, the first layer of the plurality of layers may be the upper layer of the plurality of layers as described above, and the second layer of the plurality of layers may be the lower layer of the plurality of layers as described above.

The buffer channel may be an elongated recess or through-hole disposed on a layer of the plurality of layers. In a different example, the buffer channel may be a tunnel or a channel embedded in this layer.

The buffer channel and the sample channel 212 may be fluidly connected to each other by a through-hole.

The through-hole may include a rectangle-shaped through-hole arranged lengthwise across a width of the buffer channel and/or the width of the sample channel 212. For example, the rectangle-shaped through-hole may be narrow and may have a width in a range of about 50 µm to about 500 µm.

In various embodiments, the running buffer reagent may include a preloaded running buffer gel. The preloaded running buffer gel may be a solidified gel with appropriate ionic strength for gel electrophoresis.

As described above, solidified running buffer gel in the buffer channel may prevent any bubble generated by electrodes used for electrophoresis from entering the sample channel 212, the stacking channel 214 and the separation channel 216.

In various embodiments, the microfluidic device 202 may further include a third pair of reservoirs in fluid communication with the buffer channel, wherein the third pair of reservoirs may be configured to provide a third inlet and a third outlet for a liquid running buffer reagent to be loaded in the buffer channel to form the preloaded running buffer gel.

The liquid running buffer reagent may be loaded through the third inlet and into the buffer channel by using a pipette.

Once the buffer channel is filled, the third outlet may allow the excess liquid running buffer reagent to flow out of the buffer channel.

Accordingly, various embodiments may provide separate pairs of reservoir inlet and outlet that may be used for preloading of the said different gels into the buffer channel, the stacking channel 214 and the separation channel 216. These channels and reservoirs may be located at different layers of the microfluidic device 202, and may be connected by through-holes.

In various embodiments, the microfluidic device 202 may further include at least two electrical contact points for coupling to an electrical source to provide an electrical field across the at least two electrical contact points, wherein the buffer channel, the sample channel 212, the stacking channel 214 and the separation channel 216 may be arranged between the at least two electrical contact points. This way, the electrical field may be provided for gel electrophoresis in the microfluidic device 202.

The at least two electrical contact points may be provided in the reservoirs, for example, at the third inlet of the buffer channel and at the second inlet of the separation channel 216, which may be located at extreme ends of the microfluidic device 202. The at least two electrical contact points may provide as electrodes for electrophoresis. With the electrodes placed in the buffer channel, a sample would not directly contact with these electrodes and this may reduce or eliminate any possible damage or adsorption of a loaded sample to the electrodes.

In various embodiments, the reservoir serving as the second inlet of the separation channel 216 may include the running buffer reagent.

In various embodiments, the microfluidic device 202 may further include a plurality of main channels, each of the plurality of main channels including a buffer channel, a sample channel, a stacking channel and a separation channel in fluid communication with one another. Each main channel may be arranged substantially parallel to an adjacent main channel.

In various embodiments, the microfluidic device 202 may further include at least two electrical contact points for coupling to an electrical source to provide an electrical field across the at least two electrical contact points, wherein the plurality of main channels may be arranged between the at least two electrical contact points. In this case, the buffer channels of the plurality of main channels may be connected to one of the at least two electrical contact points, and the separation channels of the plurality of main channels may be connected to the other of the at least two electrical contact points.

In other words, the microfluidic device 202 may contain multiple channels with each set of channels for each sample. The multiple channels may be identical. In one example, each channel may have its own two reservoirs for loading of electrodes. In another example, the multiple channels may share the same pair of electrical contact points. The multiple channels for the test (loaded) sample and the preloaded stacking reagent 204 may be isolated by the multiple channels for the running buffer reagent and the preloaded separation reagent 206. The multiple channels for the running buffer reagent may be connected with one electrical contact point, while the multiple channels for the preloaded separation reagent 206 may be connected with the other electrical contact point.

Figure 2B:
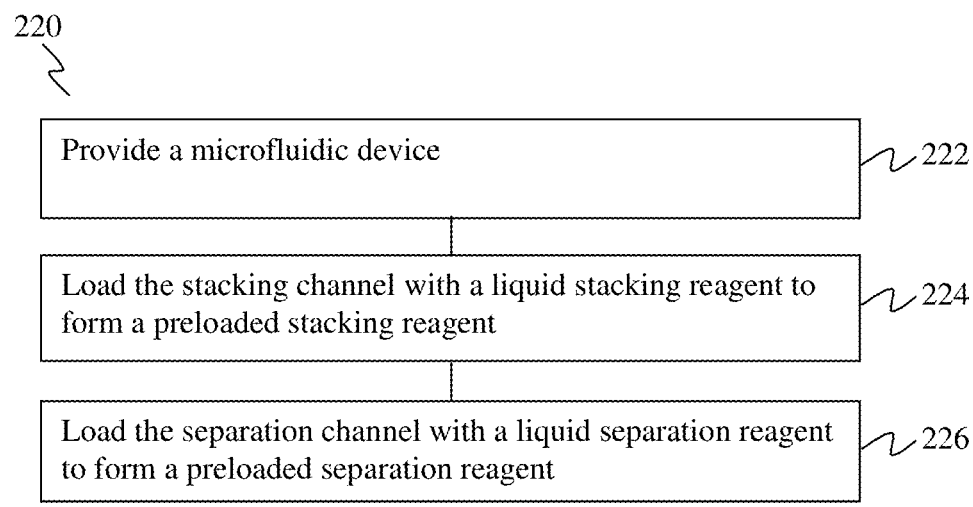
FIG. 2B shows a flow chart illustrating a method of manufacturing a microfluidic device for gel electrophoresis, according to various embodiments.

FIG. 2B shows a flow chart 220 illustrating a method of manufacturing a microfluidic device for gel electrophoresis. At 222, a microfluidic device is provided. The microfluidic device includes a sample channel configured to receive a sample; a stacking channel; and a separation channel, wherein the sample channel, the stacking channel and the separation channel are in fluid communication with one another. At 224, the stacking channel is loaded with a liquid stacking reagent to form a preloaded stacking reagent. At 226, the separation channel is loaded with a liquid separation reagent to form a preloaded separation reagent. The preloaded stacking reagent has a physical characteristic different from that of the preloaded separation reagent.

The microfluidic device may include the same or like elements or components as those of the microfluidic device 202 of FIG. 2A, and as such, the like elements may be as described in the context of the microfluidic device 202 of FIG. 2A, and therefore the corresponding descriptions are omitted here.

In various embodiments, in the step of providing the microfluidic device 222, the microfluidic device may further include a buffer channel, wherein the buffer channel may be in fluid communication with the sample channel. The method may further include loading the buffer channel with a running buffer reagent to form a preloaded buffer reagent, wherein the preloaded buffer reagent has a physical characteristic different from that of the preloaded stacking reagent and the preloaded separation reagent.

In various embodiments, prior to the step of providing the microfluidic device 222, the method may further include forming the stacking channel and the separation channel on different layers of a plurality of layers of the microfluidic device. The method may also include forming the buffer channel in a layer of the plurality of layers of the microfluidic device.

The method may further include coupling or bonding the plurality of layers together. This may be carried out by using thermal bonding, laser welding, adhesive bonding, and any other suitable methods.

The method may further include forming through-holes across adjacent layers. By doing so, the stacking channel and the separation channel may be fluidly connected to each other by a through-hole, and the sample channel and the stacking channel may be fluidly connected to each other by another through-hole. The buffer channel and the sample channel may be fluidly connected to each other by a different through-hole.

In various embodiments, after providing the microfluidic device at 222, the buffer channel may be loaded with a liquid running buffer reagent.

In one embodiment, the liquid running buffer reagent may be allowed to solidify and form a running buffer gel.

In various embodiments, the method may further include providing at least two electrical contact points for coupling to an electrical source to provide an electrical field across the at least two electrical contact points.

Accordingly, various embodiments may provide a fabrication technique to manufacturing a microfluidic device for gel electrophoresis, consisting of: at least two electrical contact points; a running buffer gel channel (e.g., the buffer channel) filled with a first type of gel (e.g., the running buffer reagent or gel) connecting to a first waste reservoir; a first channel connecting to the said running buffer gel channel (e.g., the buffer channel) with an inlet for loading a first type of liquid gel (e.g., the running buffer reagent); a sample channel for loading samples; a stacking channel prefilled with a second gel (e.g., the stacking reagent) connecting to a second waste reservoir; a second channel connecting to the said stacking channel with an inlet for filling a second liquid gel (e.g., the stacking reagent); a separation channel prefilled with a third gel (e.g., the separation reagent) connecting to a third waste reservoir; a third channel connecting to the said separation channel with an inlet for filling a third liquid gel (e.g., the separation reagent). The structures may be firstly formed by laser ablation, milling, injection molding, and any other suitable techniques on plates for interlayers; the said plates and a top layer and a bottom layer may be bonded together by thermal, laser welding, adhesive bonding, and any other suitable methods; the said second liquid gel reagent (e.g., the stacking reagent) may move from the said second channel to the said stacking gel channel to the said second waste reservoir; the said second liquid gel reagent (e.g., the stacking reagent) may be solidified in a given time period; the said first liquid gel reagent (e.g., the running buffer reagent) may move from the said first channel to the said running buffer channel (e.g., the buffer channel) to the said first waste reservoir; the said third liquid gel reagent (e.g., the separation reagent) may move from the said third channel to the said separation channel to the said third waste reservoir; the said first liquid gel reagent (e.g., the running buffer reagent) and the said third liquid gel reagent (e.g., the separation reagent) solidified in a given time period.

While the method described above is illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

Non-limiting illustrative examples of microfluidic devices for gel electrophoresis in accordance with various embodiments are described below.

Figure 3A:
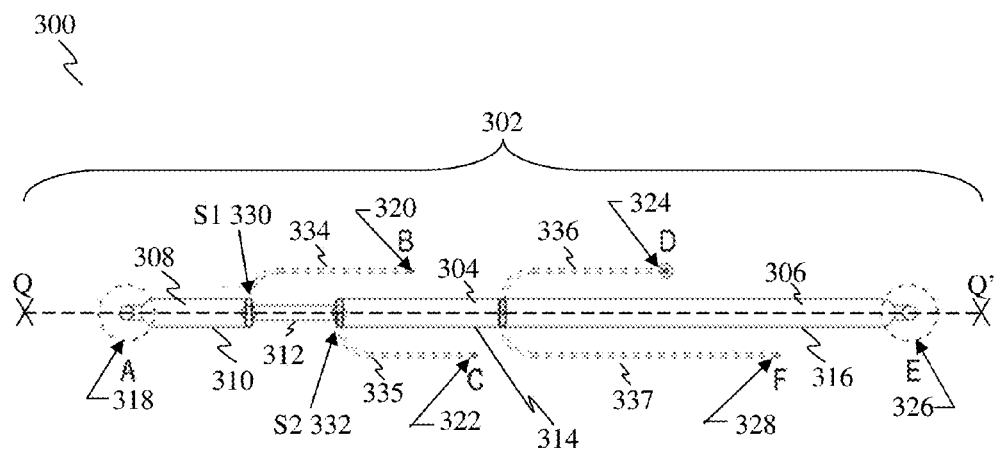
FIG. 3A shows a schematic top view of a gel preloaded microfluidic device with a single main channel, according to various embodiments.
Figure 3B:
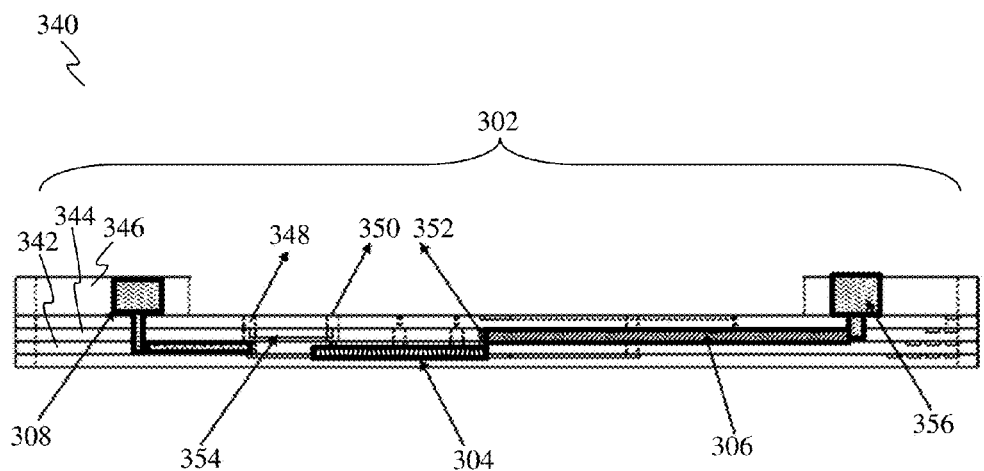
FIG. 3B shows a schematic cross sectional view of the gel preloaded microfluidic device of the embodiment of FIG. 3A taken along the line Q-Q'.

FIG. 3A shows a schematic top view 300 of a gel preloaded microfluidic device 302 with a single main channel in accordance with various embodiments, while FIG. 3B shows a schematic cross-sectional side view 340 of the microfluidic device 302 as seen from line Q-Q' of FIG. 3A. In FIGS. 3A and 3B, the microfluidic device 302 has a stacking gel 304, a separation gel 306, and a running buffer gel 308 that are preloaded into respective channels 314, 316, 310 at different layers 342, 344 linked by through-holes 348, 350, 352.

As described herein and in the context of various embodiments, the gel preloaded microfluidic device 302 may interchangably mean a microfluidic device, a microfluidic chip, a reagent preloaded microfluidic chip, or simply a reagent preloaded chip.

Characteristics of the gel preloaded microfluidic device 302 are discussed as follow.

The gel preloaded microfluidic device 302 may be preloaded with the stacking gel 304, the separation gel 306, and the running buffer gel 308.

Separate pairs of reservoir inlet and outlet may be used for preloading of the said different gels into respective channels. As shown in FIG. 3A, reservoirs A 318 and B 320 are for preloading of the running buffer gel 308, reservoirs C 322 and D 324 are for preloading of the stacking gel 304, reservoirs E 326 and F 328 are for preloading of the separation gel 306.

Some of the reservoirs may be coupled to respective channels via connecting channels. For example, reservoir B 320 may be coupled to a running buffer channel 310 via a connecting channel 334, reservoirs C 322 and D 324 may be coupled to a stacking gel channel 314 via a connecting channel 335 and a connecting channel 336, respectively, and reservoir F 328 may be coupled to a separation gel channel 316 via a connecting channel 337.

Reservoirs A 318 and E 326 may be located in an overlying top layer 346. Other reservoirs and the connecting channels may be located on layers different from the layers on which the respective channels (the running buffer channel 310, the stacking gel channel 314, the separation gel channel 316) may be arranged.

A channel 312 between reservoirs S1 330 and S2 332 may be for a test sample 354 to be loaded at the point of use. The loading of the test sample 354 may be done by means of a pipette (not shown in FIGS. 3A and 3B). In other words, the channel 312 may be accessible by a pipette and the loading of the test sample 354 may be carried out by directly dispensing the test sample 354 out of the pipette and into the channel 312.

The running buffer gel 308 preloaded into the running buffer channel 310 may be used behind the sample channel 312. In other words, the running buffer gel channel 310 may be located upstream with respective to the sample channel 312. The running buffer gel 308 may be prepared as a solidified gel form which has appropriate ionic strength. The running buffer gel 308 may enable the prevention of the air bubbles being generated by electrolysis, that are found when using standard running buffer solution, from entering the main channel (e.g., the running buffer gel channel 310, a stacking gel channel 314 and a separation gel channel 316). In the event where once the air bubbles enter the main channel, these bubbles may cause high resistance and reduce the electrical current in the main channel, which may then slow down or even stop the moving of the test sample 354 during electrophoresis. In the microfluidic device 302 as seen in FIGS. 3A and 3B, the stacking gel channel 314 and a separation gel channel 316 are arranged downstream with respective to the sample channel 312.

The gels 304, 306, 308 may be preloaded on different layers 342, 344, yet linked together by strategically located through-holes 348, 350, 352. The through-holes 348, 350, 352 may be strategically located to enable smooth connectivity between adjacent channels and to enable the loaded sample in a particular channel to optimally experience the working function of that channel. For example, the through-hole 352 may be located at an extreme end (entry) of the separation gel channel 316 and may be linked to an extreme end (exit) of the stacking gel channel 314. This way, the entire length of the separation gel 306 may be used for separation.

The running buffer gel 308 and the stacking gel 304 may be located at a same layer 342 that may be lower than or beneath the layer 344 in which the sample channel 312 may be located. This arrangement may effectively partition the different gels (including the testing sample 354) with minimized diffusion of molecules in the reagents (FIG. 3B).

The gel preloaded microfluidic device 302 contains two electrical contact points at reservoirs A 318 and E 326, where the running buffer gel 308 and a running buffer gel 356 may be respectively preloaded. In an alternative example (not shown in the figures), a running buffer may be loaded at the point of use.

The gel preloaded microfluidic device 302 may be described in similar context to the microfluidic device 202 of FIG. 2A. Accordingly, the running buffer gel channel 310, the sample channel 312, the stacking gel channel 314, the separation gel channel 216, the running buffer gel 308, the stacking gel 304, and the separation gel 306 may be described in similar context to the buffer channel as described in various embodiments, the sample channel 212, the stacking channel 214, the separation channel 216, the running buffer reagent as described in various embodiments, the preloaded stacking reagent 204, and the preloaded separation reagent 206, respectively.

Figure 4A:
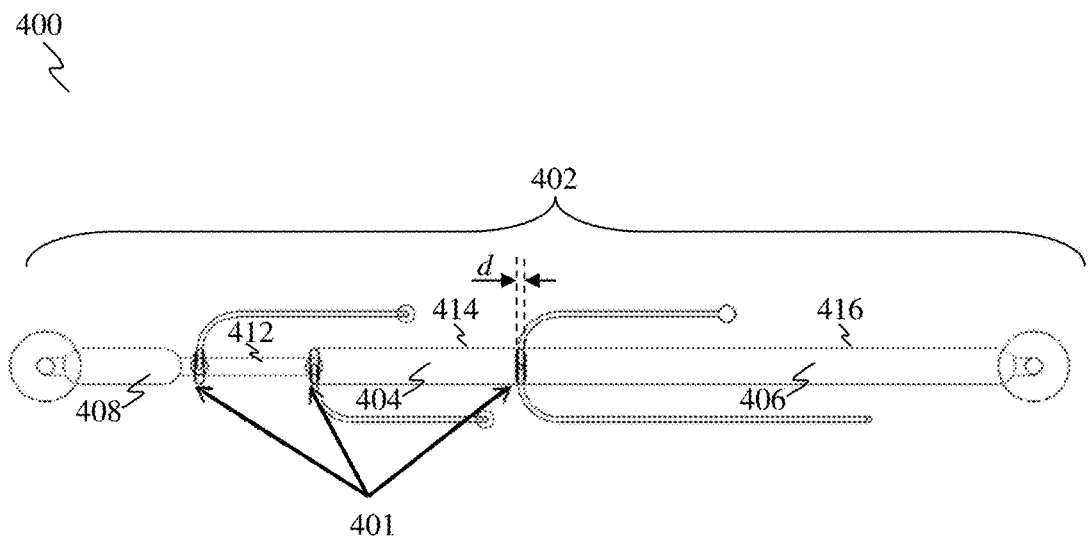
FIG. 4A shows schematic top views of (i) a microfluidic device with narrow rectangle-shaped through-holes, and (ii) a microfluidic device with round-shaped through-holes, according to various embodiments.
Figure 4A:
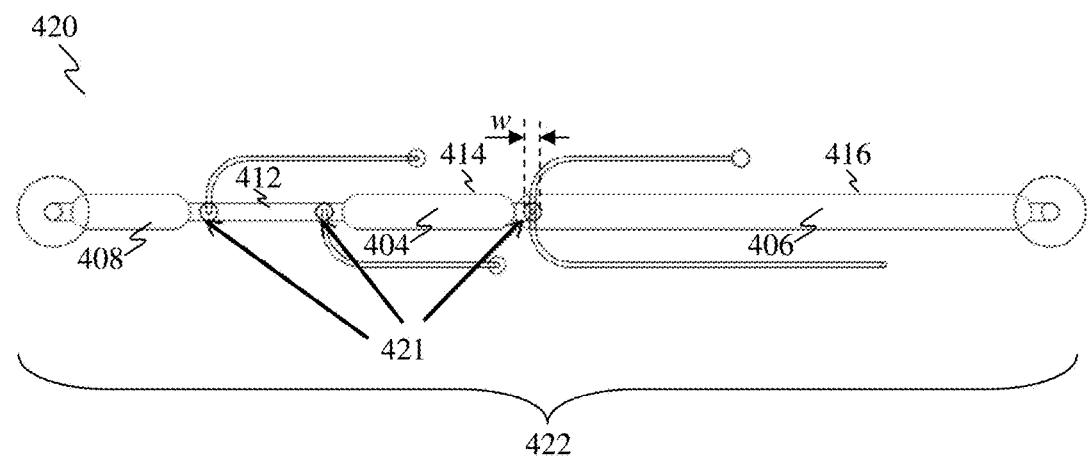

In other embodiments, narrow rectangle-shaped through-holes across the channel width may be used to link different layer of channels. FIG. 4A shows schematic top views 400, 420 of (i) a microfluidic device 402 with narrow rectangle-shaped through-holes 401, and (ii) a microfluidic device 422 with round-shaped through-holes 421, in accordance with various embodiments.

In FIG. 4A (i), the typical width d of each of the rectangle-shaped through-holes 401 may be in the range of about 50 μm to about 500 μm, but may be configurable in even smaller sizes. In FIG. 4A (ii), the typical diameter w of each of the round-shaped through-holes 421 may be in the range of about 50 μm to about 500 μm, but may be configurable in even smaller sizes.

Once a sample is loaded through a sample channel 412, appropriate electrical field may be applied. Sample proteins may be transferred into and stacked in a stacking gel channel 414 that is preloaded with a stacking gel 404, and then separated in a separation gel channel 416 that is preloaded with a separation gel 406.

For example, the stacking gel 404 may be a 200 μL stacking gel having a formulation as shown in Table 1.

TABLE 1

| Water (H$_2$O) | 119.1 μL |
| 0.5M Tri-HCl buffer, pH 6.8 | 50 μL |
| 10% (w/v) SDS | 2 μL |
| Acrylamide/Bis-acrylamide (30%/0.8% w/v) | 26.7 μL |
| 10% (w/v) ammonium persulfate (APS) | 2 μL |
| Tetramethylethylenediamine (TEMED) | 0.2 μL |

For example, the separating gel 406 may be a 400 μL separating gel having a formulation as shown in Table 2, based on various acrylamide percentages.

TABLE 2

| | Acrylamide percentage | | | | |
| --- | --- | --- | --- | --- | --- |
| | 6% | 8% | 10% | 12% | 15% |
| Water (H$_2$O) | 211.6 μL | 184.6 μL | 158.6 μL | 131.6 μL | 91.6 μL |
| Acrylamide/Bis-acrylamide (30%/0.8% w/v) | 80 μL | 107 μL | 133 μL | 160 μL | 200 μL |
| 1.5M Tri-HCl buffer, pH 8.8 | 100 μL | 100 μL | 100 μL | 100 μL | 100 μL |
| 10% (w/v) SDS | 4 μL | 4 μL | 4 μL | 4 μL | 4 μL |
| 10% (w/v) ammonium persulfate (APS) | 4 μL | 4 μL | 4 μL | 4 μL | 4 μL |
| Tetramethylethylenediamine (TEMED) | 0.4 μL | 0.4 μL | 0.4 μL | 0.4 μL | 0.4 μL |

For example, the running buffer gel 408 may be a 1× running buffer gel having a formulation as shown in Table 3.

TABLE 3

| Water (H$_2$O) | 755.7 μL |
| 10x running buffer stock solution pH 8.3 | 100 μL |
| Acrylamide/Bis-acrylamide (30%/0.8% w/v) | 133.3 μL |
| 10% (w/v) ammonium persulfate (APS) | 10 μL |
| Tetramethylethylenediamine (TEMED) | 1 μL |
| Total | 1 mL |

The microfluidic device 402 (FIG. 4A (i)) and the microfluidic device 422 (FIG. 4A (ii)) may include the same or like elements or components as those of the microfluidic device 302 of FIGS. 3A and 3B, and as such, numerals with similar end number(s) are assigned for easy referencing and the like elements may be as described in the context of the microfluidic device 302 of FIGS. 3A and 3B, and therefore the corresponding descriptions are omitted here.

Figure 4B:
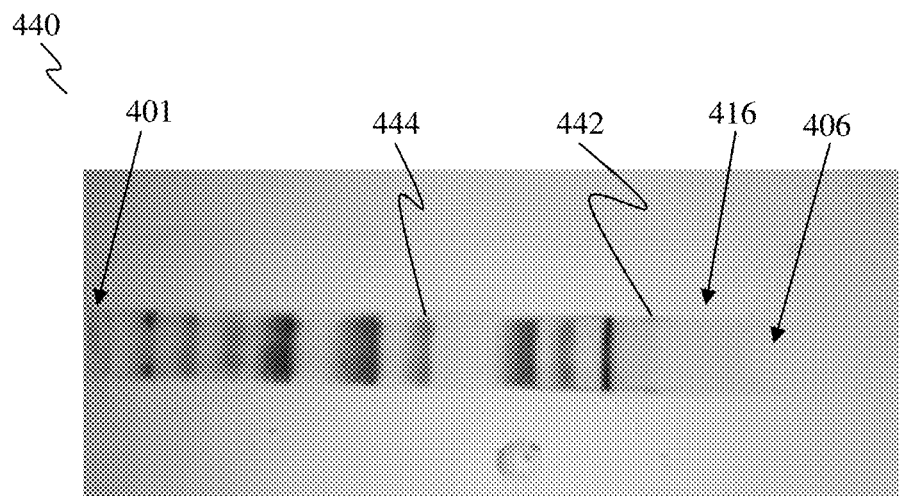
FIG. 4B shows images of the separation results of gel electrophoresis when using (i) the microfluidic device with narrow rectangle-shaped through-holes, and (ii) the microfluidic device with round-shaped through-holes of the respective embodiments of FIG. 4A.
Figure 4B:
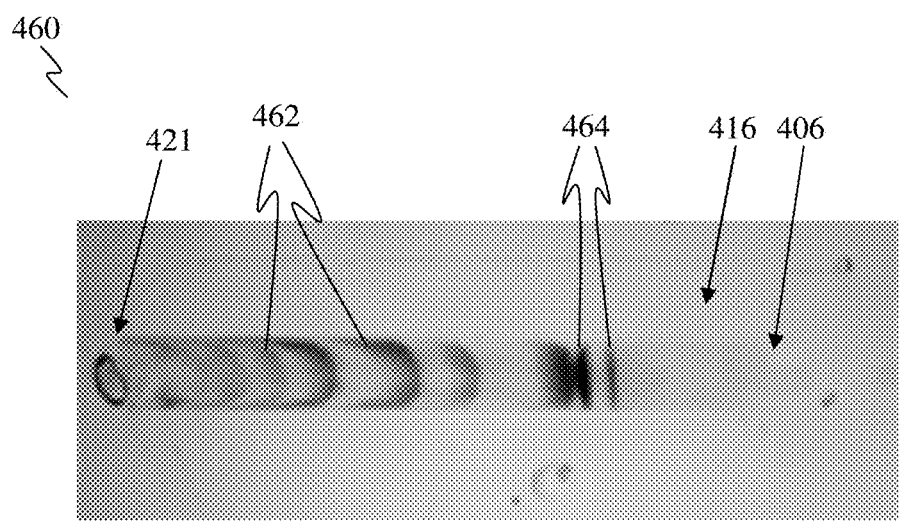

It is noted that the shape of the through-holes may affect the shape of separated protein bands and therefore the separation performance. FIG. 4B shows images 440, 460 of the separation results of gel electrophoresis when using (i) the microfluidic device 402 with narrow rectangle-shaped through-holes 401 (FIG. 4A (i)), and (ii) the microfluidic device 422 with round-shaped through-holes 421 (FIG. 4A (ii)). Protein standards from Bio-Rad Laboratories, Inc. (US), having molecular masses of 10 to 250 KDa, may be used in a sample loaded into the sample channel 412 for the gel electrophoresis.

The protein bands seen in FIG. 4B (i) are susbtantially linear, and distinctively separated from one another. The position of each protein band may correspond to proteins of a particular molecular weight, and the intensity of the protein band may reflect the concentration of proteins of that particular molecular weight. For example, the protein band 442 may be considered having a substantially furthest distance away from the narrow rectangle-shaped through-hole 401 arranged between the stacking gel channel 414 (not shown in FIG. 4B (i)) and the separation gel channel 416. In this example, the protein band 442 may represent 10 kDa proteins.

It may also be observed from FIG. 4B (i) that proteins in a sample exit from the narrow rectangle-shaped through-hole 401 at about the same time and into the separation gel channel 416. Since proteins having the same molecular weight have substantially the same mobility, these proteins may diffuse into the separation gel 406 at substantially similar rates to form a linear protein band (e.g., the protein band 442) in the separation gel 406. Proteins having a different molecular weight may also diffuse into the separation gel 406 at substantially similar rates to form a different linear protein band (e.g., protein band 444) in the separation gel 406.

Meanwhile, the protein bands seen in FIG. 4B (ii), especially the protein bands 462 located nearer to the round-shaped through-hole 421 have curved edges that are shaped similarly conforming to part of the circumference of the round-shaped through-hole 421. It may also be observed from FIG. 4B (ii) that proteins in a sample exit from the round-shaped through-hole 421 at different times and into the separation gel channel 416. Since proteins having the same molecular weight have substantially the same mobility, these proteins may initially diffuse into the separation gel 406 at substantially similar rates to form a curved protein band in the separation gel 406, for example, as in protein bands 462 as these proteins exit from the round-shaped through-hole 421 at different times. As proteins having lower molecular weights may migrate further away from the round-shaped through-hole 421, the difference between the time which some of these proteins exit from the round-shaped through-hole 421 may be compensated by the mobility of these proteins in the separation gel 406 to form substantially more linear protein bands 464.

Figure 5:
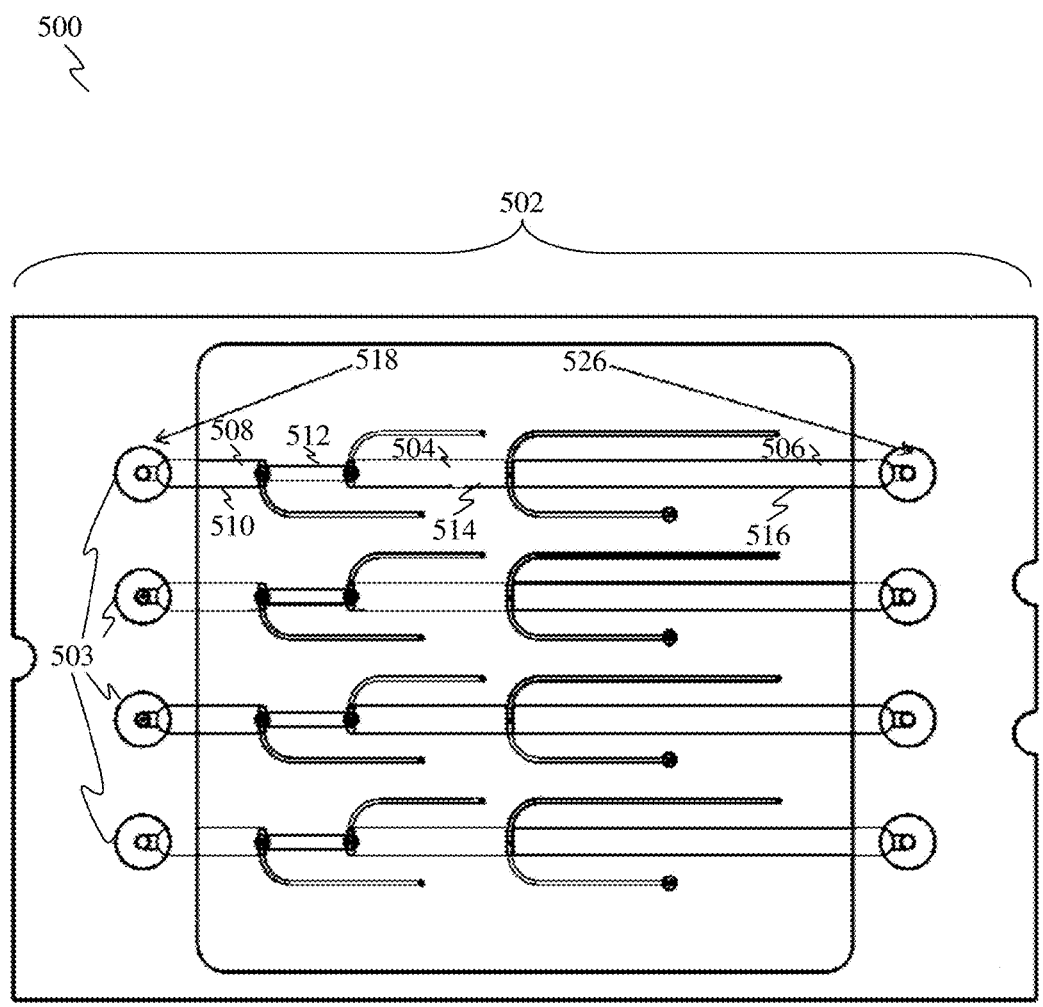
FIG. 5 shows a schematic top view of a microfluidic device for testing four samples, according to one embodiment.

In another embodiment, multiple parallel main channels may be used for on-chip gel electrophoresis of multiple samples. For example, FIG. 5 shows a schematic top view 500 of a microfluidic device 502 for testing four samples. As seen in FIG. 5, four identical or at least susbstantially similar main channels 503 are arranged at least substantially parallel to one another on the microfluidic device 502. Each main channel 503 may include a running buffer gel channel 510 preloaded with a running buffer 508, a sample channel 512, a stacking gel channel 514 preloaded with a stacking gel 504, and a separation gel channel 516 preloaded with a separation gel 506. Each main channel 503 of the microfluidic device 502 (FIG. 5) may include the same or like elements or components as those of the microfluidic device 302 of FIGS. 3A and 3B, or the microfluidic device 402, 422 (FIG. 4A), and as such, numerals with similar end number(s) are assigned for easy referencing and the like elements may be as described in the context of the microfluidic device 302 of FIGS. 3A and 3B, or the microfluidic device 402, 422 (FIG. 4A), and therefore the corresponding descriptions are omitted here.

Each main channel 503 may be used for one sample. Each main channel 503 may have its own two running buffer reservoirs 518, 526 for loading of electrodes or electrical contact points (not shown in FIG. 5). The multiple channels 503 may be used simultaneously or separately according to different testing requirements. The number of the channels 503 may be further added when needed.

Figure 6:
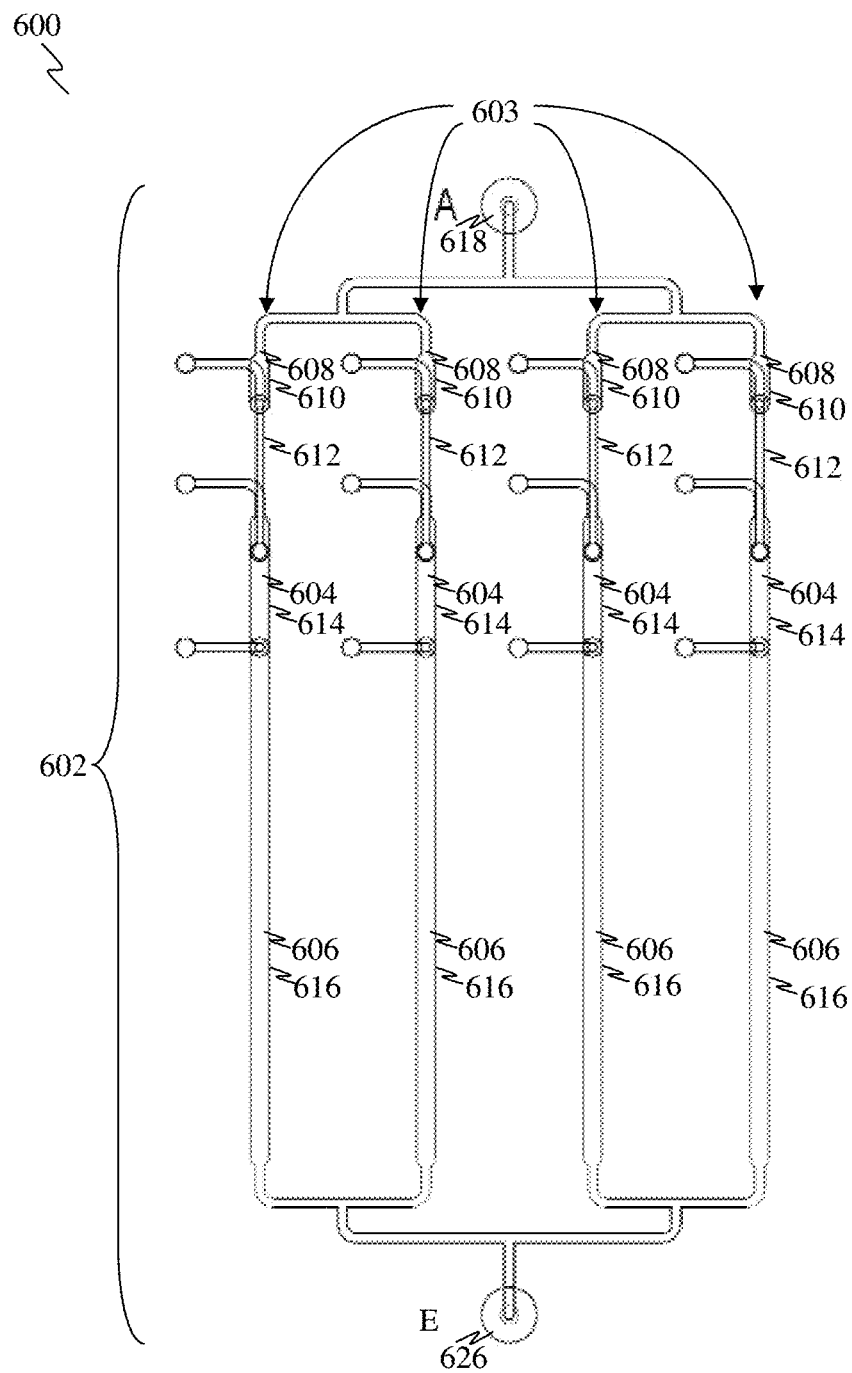
FIG. 6 shows a schematic top view of a microfluidic device for testing four samples, according to another embodiment.

In yet another embodiment, multiple parallel main channels may be connected with the same pair of reservoirs. FIG. 6 shows a schematic top view 600 of a microfluidic device 602 with four parallel sample channels 612 that are isolated by running buffer gel channels 610 preloaded with a running buffer 608 (connected to the same reservoir A 618) and respective stacking gel channels 614 preloaded with a stacking gel 604. Each main channel 603 of the microfluidic device 602 (FIG. 6) may include the same or like elements or components as those of the microfluidic device 302 of FIGS. 3A and 3B, or the microfluidic device 402, 422 (FIG. 4A), and as such, numerals with similar end number(s) are assigned for easy referencing and the like elements may be as described in the context of the microfluidic device 302 of FIGS. 3A and 3B, or the microfluidic device 402, 422 (FIG. 4A), and therefore the corresponding descriptions are omitted here.

Each sample channel 612 may be for one sample. Respective separation gel channels 616 preloaded with a separation gel 606 may be connected with the same reservoir E 626. After applying an electrical field between reservoirs A 618 and E 626 using one pair of electrodes or electrical contact points (not shown in FIG. 6), the samples may be transferred, stacked and separated in the respective stacking gel channels 614 and separation gel channels 616 as described above. The number of the main channels 603 may be further added when needed.

The microfluidic device in accordance with various embodiments may include running buffer gel channel(s), sample channel(s), stacking gel channel(s), and separation gel channel(s) that may be in the micrometer scale (e.g., microchannels). The size of a microchannel containing a gel is generally significantly smaller as compared to the components for conventional SDS-PAGE. Therefore, significantly reduced amounts of reagents may used, and this may significantly reduce the cost of conducting gel electrophoresis using the microfluidic device in accordance to various embodiments as compared to conventional SDS-PAGE.

Table 4 shows the amounts of reagents required for preloading operation of the the microfluidic device in accordance to various embodiments as compared to conventional gel (e.g., conventional SDS-PAGE), based on 10 testing samples.

TABLE 4

| Reagents needed (ml) | Conventional gel | Microfluidic device | % reduction |
| --- | --- | --- | --- |
| Separation gel | 5 | 0.4 | 92.0 |
| Stacking gel | 1 | 0.2 | 80.0 |
| Running buffer gel | 700 | 1 | 99.8 |

As seen from Table 4, more than 80% reduction in reagent consumption may be observed when using the microfluidic device in accordance to various embodiments.

Figure 7A:
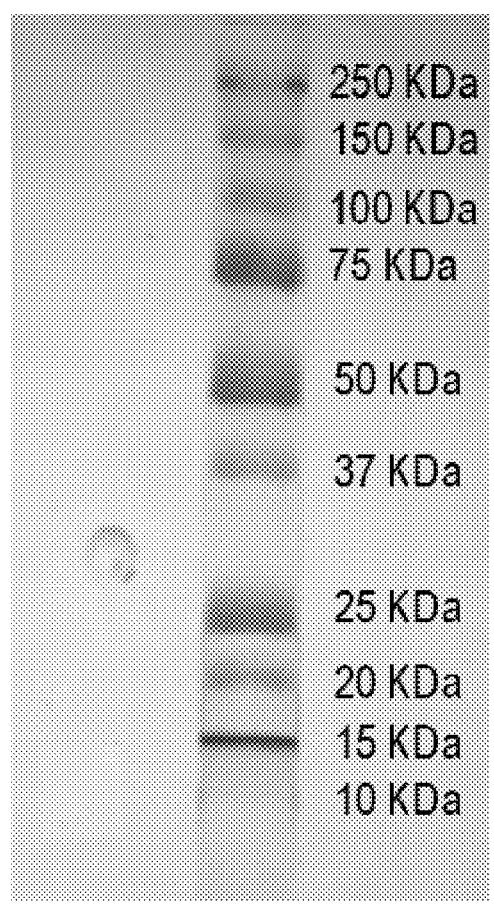
FIG. 7A shows an image illustrating separated protein bands in a separation channel of a microfluidic device, according to various embodiments.

Pre-stained protein standards (from Bio-Rad Laboratories, Inc. (US)) containing proteins with molecular masses of about 10 to 250 KDa may used to test the separation performance of the microfluidic device in accordance to various embodiments. FIG. 7A shows an image 700 illustrating the separated protein bands in the separation channel of the microfluidic device. As shown in FIG. 7A, the proteins of 10 different molecular weights of the protein standards may be observed to be totally separated from one another after performing gel electrophoresis for 15 minutes at 300 V.

Figure 7B:
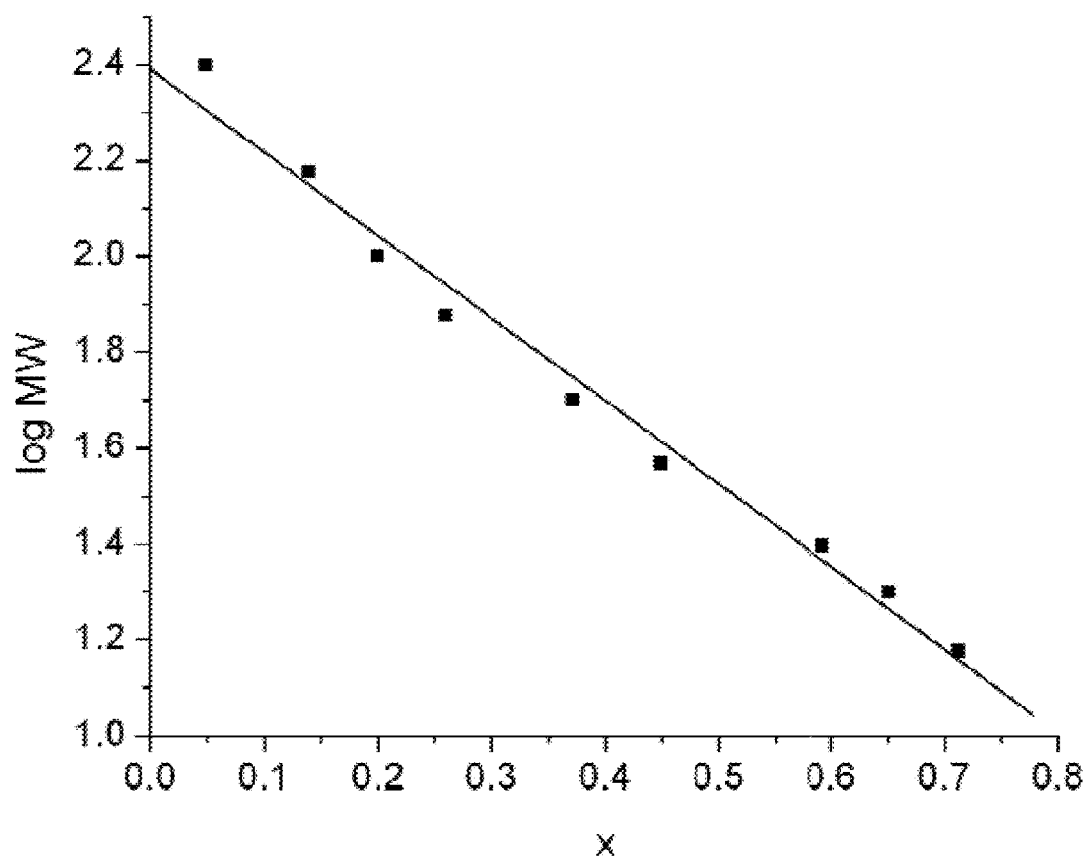
FIG. 7B shows a plot illustrating log MW (molecular weight) of the tested protein standards versus the relative migration distance of respective protein bands of FIG. 7A.

FIG. 7B shows a plot 720 illustrating log MW of the tested protein standards versus the relative migration distance of respective protein bands. In FIG. 7B, the regression of the relative migration distance to the Log MW of the 10 standard proteins forms a straight least square line as represented by Equation 1 to give (Log MW=−1.773x+2.401, R=0.9929) where x is the mobility and R is the least square error. With this, the reagent preloaded microfluidic device in accordance with various embodiments may be used for separation of proteins based on their MW and determination of molecular weight of some unknown proteins.

The reagent preloaded microfluidic device in accordance with various embodiments may be manufactured according to the process as described below.

First, structures may be formed by laser ablation, milling, injection molding, and any other suitable techniques on plates for interlayers according to the channel (microchannel) design.

Second, these plates may be bonded together by thermal bonding, laser welding, adhesive bonding, and any other suitable methods. These plates may be arranged between an overlying top layer and an underlying bottom layer which may also be bonded to the plates. The plates may interchangeably be referred herein as layers (e.g., layers 342, 344 of FIG. 3B). For example, the underlying bottom layer may form a base over which an adjacent layer (e.g., layer 342 of FIG. 3B) may be laid, and the overlying top layer (e.g., layer 346 of FIG. 3B) may contain structures faciliating as reservoirs for running buffer gels.

Figure 8A:
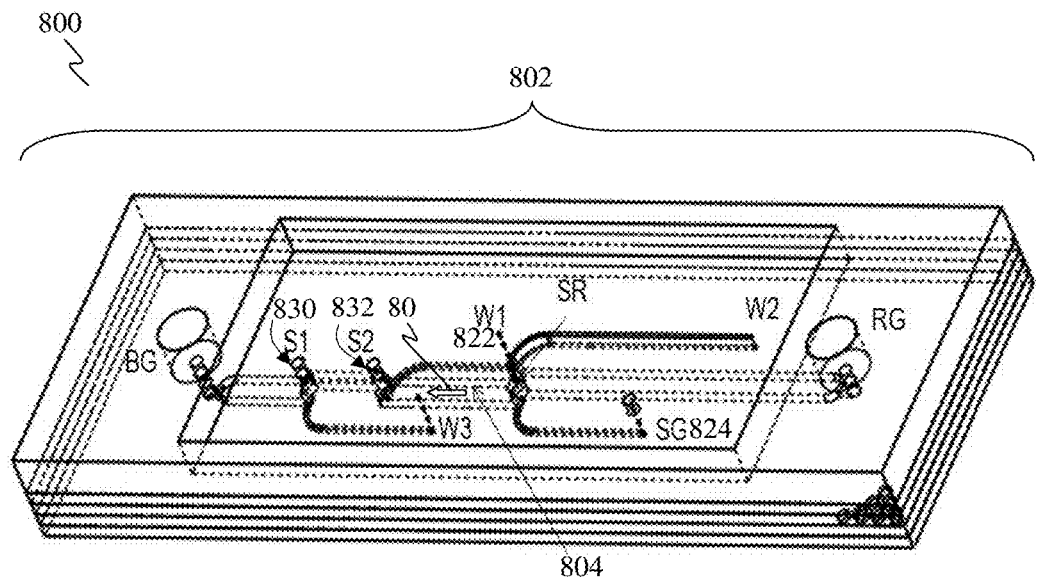
FIGS. 8A and 8B show schematic views illustrating the reagent prefilling or preloading process for a bonded microfluidic device, according to various embodiments.
Figure 8B:
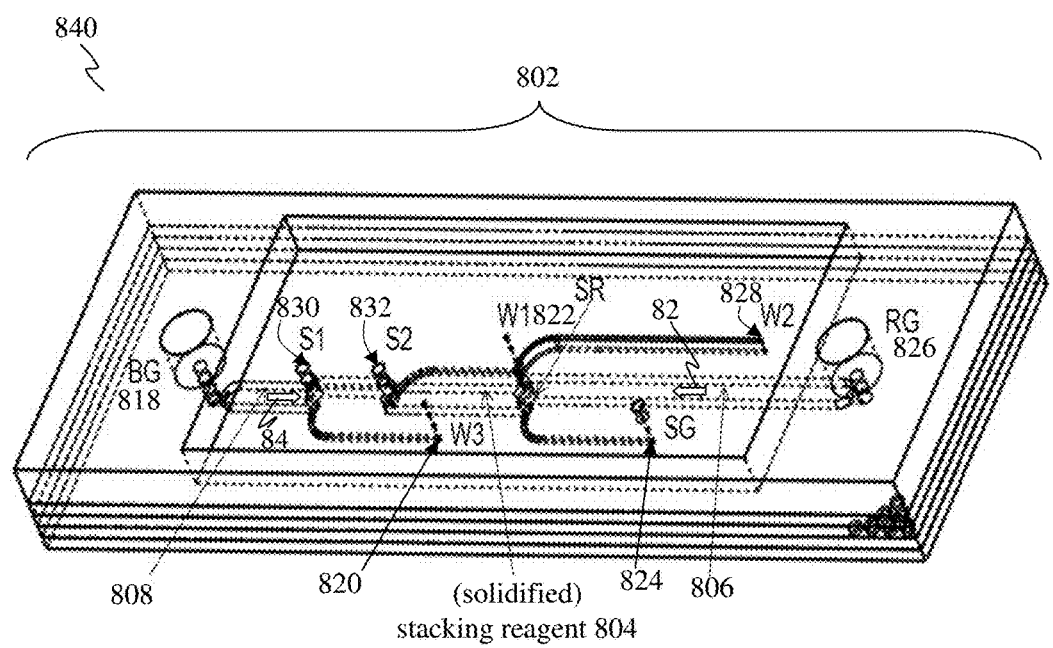

Following that, various reagents may be prefilled into different parts of the bonded device. FIGS. 8A and 8B show schematic views 800, 840 illustrating the regent prefilling or preloading process for the bonded microfluidic device 802 in accordance with various embodiments.

The bonded microfluidic device 802 may include the same or like elements or components as those of the microfluidic device 302 of FIGS. 3A and 3B, or the microfluidic device 402, 422 (FIG. 4A), and as such, numerals with similar end number(s) are assigned for easy referencing and the like elements may be as described in the context of the microfluidic device 302 of FIGS. 3A and 3B, or the microfluidic device 402, 422 (FIG. 4A), and therefore the corresponding descriptions are omitted here.

As shown in FIG. 8A, a liquid stacking reagent 804 may be filled from reservoir SG 824 toward waste reservoir W1 822 in a direction denoted by an arrow 80. The liquid stacking reagent 804 may be left to wait for about 5 to 10 minutes until the liquid stacking reagent 804 solidifies to form a stacking gel.

Subsequently, as shown in FIG. 8B, a liquid separation reagent 806 may be filled from reservoir RG 826 toward reservoir W2 828 in a direction denoted by an arrow 82. At the same time, a liquid running buffer reagent 808 may be filled from reservoir BG 818 toward reservoir W3 820 in a direction denoted by an arrow 84. Both the liquid separation reagent 806 and the liquid running buffer reagent 808 may be left to wait for about 5 to 10 minutes until the liquid separation reagent 806 solidifies to form a separation gel and the liquid running buffer reagent 808 solidifies to form a running buffer gel.

In FIGS. 8A and 8B, reservoirs S1 830 and S2 832 may be described in similar context with respect to reservoirs S1 330 and S2 332 of FIG. 3A, between which a sample channel may be arranged for a test sample to be loaded at the point of use.

The microfluidic device in accordance with various embodiments may provide the following features.

Multi-layer of channel network to perform gel electrophoresis on chip with sample-in-results-out may be provided. No chip preparation and reagents loading may be required for users. Separate pairs of reservoir inlet and outlet may used for preloading of different gels into respective channels. A running buffer gel may be used behind the sample channel. It may be prepared as a solidified gel form having the appropriate ionic strength. It may prevent the air bubbles generated by electrolysis from entering a main channel. The gels may be preloaded on different layers, yet linked together by strategically located through-holes. Narrow rectangular-shaped through-holes across the channel width may improve the separation performance. The location of the running buffer gel and a stacking gel may be lower than a sample channel. This arrangement may effectively partition the different gels (including a testing sample) with minimized diffusion of molecules in the reagents. Networks of smaller channels at different layers from the main application channels may be used to facilitate the manufacturing process of gel reagents filling. The process for gel reagents filling may ensure the quality and bubble-free characteristics of the preloaded microchannels.

The microfluidic device in accordance with various embodiments may be applied in areas of industrial application including biomedical, chemistry, biochemistry, and biology.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A microfluidic device for gel electrophoresis, comprising:
    a sample channel configured to receive a sample;
    a stacking channel comprising a preloaded stacking reagent; and
    a separation channel comprising a preloaded separation reagent;
    a plurality of layers; and
        a buffer channel comprising a running buffer reagent, wherein the buffer channel is in fluid communication with the sample channel;
        wherein the preloaded stacking reagent has a physical characteristic different from that of the preloaded separation reagent;
        wherein the stacking channel and the separation channel are arranged on different layers of the plurality of layers; and
        wherein the sample channel, the stacking channel and the separation channel are in fluid communication with one another.

2. The microfluidic device of claim 1, wherein the preloaded stacking reagent has the physical characteristic of at least one of a pH level or an average pore size different from that of the preloaded separation reagent.

3. The microfluidic device of claim 1, wherein each of the stacking channel and the separation channel is a closed channel that is prevented from exposure to air.

4. The microfluidic device of claim 1, wherein the stacking channel and the separation channel are fluidly connected to each other by a through-hole.

5. The microfluidic device of claim 4, wherein the through-hole comprises a rectangle-shaped through-hole arranged lengthwise across a width of the separation channel.

6. The microfluidic device of claim 1, wherein the stacking channel and the separation channel are arranged downstream with respect to the sample channel.

7. The microfluidic device of claim 1, further comprising a first pair of reservoirs in fluid communication with the stacking channel; and a second pair of reservoirs in fluid communication with the separation channel,
    wherein the first pair of reservoirs is configured to provide a first inlet and a first outlet for a liquid stacking reagent to be loaded in the stacking channel to form the preloaded stacking reagent; and
    wherein the second pair of reservoirs is configured to provide a second inlet and a second outlet for a liquid separation reagent to be loaded in the separation channel to form the preloaded separation reagent.

8. The microfluidic device of claim 1, further comprising a plurality of layers, wherein the buffer channel and the sample channel are arranged on different layers of the plurality of layers.

9. The microfluidic device of claim 8, wherein the sample channel is arranged on a first layer of the plurality of layers, and the buffer channel is arranged on a second layer of the plurality of layers; and wherein the first layer is arranged over the second layer.

10. The microfluidic device of claim 8, wherein the buffer channel and the sample channel are fluidly connected to each other by a through-hole.

11. The microfluidic device of claim 1, wherein the sample channel is arranged between the buffer channel and the stacking channel.

12. The microfluidic device of claim 1, wherein the running buffer reagent comprises a preloaded running buffer gel.

13. The microfluidic device of claim 12, further comprising a third pair of reservoirs in fluid communication with the buffer channel,
wherein the third pair of reservoirs is configured to provide a third inlet and a third outlet for a liquid running buffer reagent to be loaded in the buffer channel to form the preloaded running buffer gel.

14. The microfluidic device of claim 1, further comprising at least two electrical contact points for coupling to an electrical source to provide an electrical field across the at least two electrical contact points, wherein the buffer channel, the sample channel, the stacking channel and the separation channel are arranged between the at least two electrical contact points.

15. The microfluidic device of claim 1, further comprising a plurality of main channels, each of the plurality of main channels comprising a buffer channel, a sample channel, a stacking channel and a separation channel in fluid communication with one another.

16. The microfluidic device of claim 15, further comprising at least two electrical contact points for coupling to an electrical source to provide an electrical field across the at least two electrical contact points, wherein the plurality of main channels are arranged between the at least two electrical contact points.

17. A method of manufacturing a microfluidic device for gel electrophoresis, the method comprising:
providing a microfluidic device comprising:
a sample channel configured to receive a sample;
a stacking channel;
a separation channel;
a plurality of layers; and
a buffer channel, wherein the buffer channel is in fluid communication with the sample channel;
wherein the sample channel, the stacking channel and the separation channel are in fluid communication with one another; and
wherein the stacking channel and the separation channel are arranged on different layers of the plurality of layers;
loading the stacking channel with a liquid stacking reagent to form a preloaded stacking reagent;
loading the separation channel with a liquid separation reagent to form a preloaded separation reagent; and
loading the buffer channel with a running buffer reagent to form a preloaded buffer reagent;
wherein the preloaded buffer reagent has a physical characteristic different from that of the preloaded stacking reagent and the preloaded separation reagent; and
wherein the preloaded stacking reagent has a physical characteristic different from that of the preloaded separation reagent.

* * * * *